(12) United States Patent
Brakstad et al.

(10) Patent No.: US 7,815,930 B2
(45) Date of Patent: Oct. 19, 2010

(54) FOOD AND FEED SUPPLEMENT AND ITS USE

(75) Inventors: Frode Brakstad, Porsgrunn (NO); Morten Harrington Raaholt, Larvik (NO)

(73) Assignee: Pigeon Vitality AS, Porsgrunn (NO)

( * ) Notice: Subject to any disclaimer, the term of this patent is extended or adjusted under 35 U.S.C. 154(b) by 42 days.

(21) Appl. No.: 10/596,224

(22) PCT Filed: Dec. 6, 2004

(86) PCT No.: PCT/NO2004/000374

§ 371 (c)(1), (2), (4) Date: Jun. 5, 2006

(87) PCT Pub. No.: WO2005/053423

PCT Pub. Date: Jun. 16, 2005

(65) Prior Publication Data
US 2007/0166355 A1   Jul. 19, 2007

(30) Foreign Application Priority Data
Dec. 5, 2003   (NO) .................................. 20035410

(51) Int. Cl.
*A61K 47/00* (2006.01)
*A23K 1/17* (2006.01)
(52) U.S. Cl. ...................................... 424/439; 424/442
(58) Field of Classification Search ................. 424/439, 424/442
See application file for complete search history.

(56) References Cited

U.S. PATENT DOCUMENTS

| 5,198,216 A | 3/1993 | McGee et al. |
| 5,935,625 A | 8/1999 | Hjornevik et al. |
| 2002/0150653 A1 * | 10/2002 | Bailey et al. ................... 426/72 |
| 2003/0077254 A1 | 4/2003 | Ramaekers |
| 2005/0214438 A1 | 9/2005 | McCormick |

FOREIGN PATENT DOCUMENTS

| DE | 2559569 A1 | 4/1977 |
| DE | 2559570 A1 | 4/1977 |
| EP | 0683985 B1 | 8/2002 |
| GB | 1420883 A | 1/1976 |
| ZA | 9605149 A | 1/1997 |

OTHER PUBLICATIONS

Food and Nutrition Board, Institute of Medicine, National Academies, Dietary Reference Intakes (DRIs);Estimated Average Requirements for Groups, 2002, National Academy of Sciences, printed from http://www.iom.edu/Object.File/Master/21/372/0.pdf, 1 page.*

Lawrence, Nutrient Requirements and Balancing Rations for Horses, Jul. 1996 preprinted 2000, Virginia Cooperative Extension-Animal and Poultry Sciences, Publication 406-473, 16 pages.*

Bianco G et al, "Clinical Observations on the Therapeutic Effect of a New Synthetic Preparation in Rheumatic Diseases" US National Library of Medicine, Nov. 17, 1970.

Rogers P J, "A Healthy Body, A Healthy Mind: Long-Term Impact of Diet on Mood and Cognitive Function" Proceedings of the Nutrition Society, London, vol. 60, No. 1, Feb. 2001, pp. 135-143, ISSN: 0029-6651.

Wolter R, "Dietetique de Cheval-Athlete" Science and Sports, Ed. Scientifiques Elsevier, Paris, FR, vol. 8, No. 2, 1993, pp. 117-126, ISSN: 0765-1597.

Taylor M H et al, "Folate for Depressive Disorders" US National Library of Medicine, 2003.

Hintikka Jukka et al, "High Vitamin B12 Level and Good Treatment Outcome May Be Associated in Major Depressive Disorder" US National Library of Medicine, Dec. 2, 2003, ISSN: 1471-244X.

Wolter R, "Dietetique de Cheval-Athlete"; Science and Sports, Ed. Scientifiques Elsevier, Paris, FR, vol. 8, No. 2, 1993, pp. 117-126, ISSN: 0765-1597.

International Search Report, date mailed Apr. 27, 2005, 3 pages.

Communication of a notice of opposition—Application No. 04808868.6 dated Jul. 12, 2009.

Vitamins in Animal Nutrition, Publisher: Arbeitsgemeinschaft fur Wirkstoffe in der Tierernahrung e.V. (AWT), 1984.

Roche Vitamin Supplementation Guidelines for Domestic Animals, 1997.

Nutrient Requirements of Poultry, National Research Council, Ninth Revised Edition, 1994.

Nutrient Requirements of Swine, National Research Council, Tenth Revised Edition, 1998.

Kirsi H. Partanen et al., Organic Acids for Performance Enhancement in Pig Diets, Nutrition Research Reviews (1999), 12, 117-145.

* cited by examiner

*Primary Examiner*—Frederick Krass
*Assistant Examiner*—Gigi Huang
(74) *Attorney, Agent, or Firm*—Brooks Kushman P.C.

(57) ABSTRACT

The present invention relates to a food and feed supplement, and its use, where the supplement comprise as the basic component at least one carboxylic acid and/or its salt, an iron component and vitamins $B_6$, $B_9$ and $B_{12}$ in amounts corresponding to at least that which theoretically can be consumed during the metabolism of the COOH-groups present. The supplement may also contain a desiccant and an antioxidant. The supplement will have a pH in the range 2.0-6.0 when dissolved in water. The supplement is characterized in that the amounts of the vitamins $B_6$, $B_9$ and $B_{12}$ are in the range of 0.5-30 mg, 0.1-10 mg and 1-1500 μg/gram dry weight of the content of the pure carboxylic acids in the supplement, respectively. The supplement can be used in animal feed in amounts of 0.5-15 grams dry supplement/kg dry feed.

10 Claims, No Drawings

FOOD AND FEED SUPPLEMENT AND ITS USE

The present invention relates to food and feed supplements comprising vitamins. The invention also comprise use of the supplement in food and feed.

It has been observed that animals exposed to severe stress or when high performance is demanded, suffer from fatigue, diarrhea, resistance to feed intake, anemia etc when they only are fed standard feed. In such cases it is obviously a need for additives or supplements to the feed. However, it is usually difficult to define what are the causes for the observed problems, and thus which additive to use. There are known numerous additives and feed supplements, but none have proved to solve all the above problems. Some additives are primarily intended for increased growth of the animal while others claim to improve its health. Vitamin deficiencies might be part of the problem, but then one should understand why this occur even when the feed is expected to contain sufficient amounts of vitamins.

A special problem has been observed on racing horses when they switch from pasture-land to intensive feeding, for instance twice a day. It is quite common that said change in feeding procedure results in development of gastric ulcer.

It is generally known that addition of monocarboxylic acids to the conventional feed can give increased growth and reduced diarrhea frequency. From EP 03176688 it is known that promoted growth of piglets can be achieved by applying conventional fodder containing 5-25% of a dry mixture containing 3-5 parts of calcium formate. However, calcium formate has a low water solubility and can only be used in limited amounts to avoid too high content of calcium in the feed. The concentration of formate in the additive is rather low and the effect is only of the same order of magnitude as when formic acid is added to the feed.

It is further known from DE 19958620 a food or food supplements for domestic or working animals applied for preventing conditions associated with vitamin deficiencies and also containing mussel meat or extracts. According to this patent said supplement should contain a number of components like soya oil, carbohydrates, minerals and various vitamins. However, the vitamins are not specified and it is difficult to decide what special problems this supplement should solve. From WO 96/35337 it is further known animal feed additives and feedstuff containing 0.2-2.5 weight % of additives comprising di-compounds of formic salts. The additive comprises 20-99 weight % potassium diformate, 0-50 weight % sodium di/tetra-formate, 0-25 weight % calcium formate, 0-4 weight % desiccant and 0-5 weight % water. This additive is stated to promote growth and improve feed conversion rate, especially during the prestarter period. The influence on diarrhea frequency is also stated to be positive.

Regarding use of organic acids in pigeon feed and risk for anemia, this is mentioned in the book "Champions Reveal their untold secrets" by Victor Vansalen, Herman International Publications, Antwerpen, Belgium. ISBN no. 90-73663-07-5. This book is central within the field of pigeon sport and reveal experiences from those working with pigeons. Their opinions about the various feed and feed additives vary considerably. There is for instance on page 68 stated that it is known to use organic acids like citric acid and ascorbic acid (vitamin C) in the feed for pigeons, but that especially acetic acid, being one of several actual acids, should not be used as it might lead to anemia. It is not specifically mentioned other organic acids in this book and what possible positive effects they might give. Further in this book, not only vitamin B, but also vitamins A, D and E are recommended as additives to pigeon feed. Accordingly there is no clear conclusions from those knowing the field of pigeon sport and breeding.

The main object of the present invention was to arrive at a new food and feed supplement that would improve health and performance, especially during stress conditions and when high performance where demanded, i.e during training and competition conditions.

Another object was to arrive at supplements that could be part of the nutrient intake of the consumer and possessing high concentration of the active ingredients and still be free flowing dry powder and stable during production, logistics, storage and handling.

It was also an object that the supplement should be water soluble, as it should be possible to add the supplement to drinking water as well as to solid powdered feed or moist feed.

A further object was to be able to supply the consumer with each of the components of the supplement and the supplement itself in predetermined dosages and still be within the specifications considered necessary for obtaining the desired effect and the supplement should have a desired taste for the consumer for eating or drinking the supplement without any refusal therefore.

From a health point of view it seemed interesting from the literature teachings to supply the nutrient consumer with supplements containing monocarboxylic acids. The inventor therefore decided to start some experiments comprising addition of monocarboxylic acid to the feed. The experiments were performed by different pigeon fanciers in Norway and Denmark, all together twenty test groups. These experiments gave positive results with regard to growth and diarrhea frequency and it all seemed promising. However, when the tested animals (pigeons) were exposed to prolonged extreme conditions, like long-distance pigeon racing it was, again observed fatigue, anemia and resistance to feed intake for some of the test groups. Obviously there were some serious side-effects from adding only carboxylic acids/salts to the feed. Fatigue can be explained by deficiencies of numerous components such as vitamin C, vitamin B-complexes, minerals like magnesium, zinc, essential fatty acids etc. The relevant literature give no clear guidance for solving the above observed problems. Just adding a mixture of various vitamins and minerals will be only speculative as long as the cause of the problem is not clear. Deficiency of vitamin $B_9$ (i.e. folic acid) could be assumed from literature definitions of the described deficiency. But similar definitions are also given for deficiency of vitamin B12. (e.g. reference Animal Nutrition, P. McDonald et al. Fifth Edition 1995, pp 80-93). However, it is also known an interaction between $B_{12}$ and $B_9$ as it seems necessary that $B_{12}$ is present in order for absorption of $B_9$, so the question will then be what vitamin should be supplemented. Some of the test groups did however perform well within the observed symptoms. During interviews of the different fanciers responsible for the test groups, the inventor got the impression that in the cases of the well performing groups the responsible fanciers had been more conscious of adding vitamin mixtures to the pigeon feed, in particular complexes of B-vitamins, than the fanciers of the poor performing groups.

Regarding the above problem with development of gastric ulcer, it was assumed that change in feeding procedure would result in imbalance in the stomach acid (HCl) of the animal and consequently lead to the development of gastric ulcer. Based on this hypothesis, it was found advantageous that the supplement, when dissolved in water, had a buffer capacity within the pH range of 2.0-6.0. Thus it was considered advantageous that the supplement comprised at least one buffer component. It was further by experiments found that the selected B-vitamins were stable for a prolonged time at said pH range provided that the supplement was not exposed to light.

It was desired to retain the advantages and positive effects of the monocarboxylic acids. The problem was to overcome the observed long-term negative effects. The inventor then decided to continue his search for a new supplement working according to a hypothesis assuming that the metabolism of the carboxylic acids somehow consumed essential vitamins. In order to try to compensate for said possible lack of vitamins, the role of vitamins in feed for various animals were studied more thoroughly. Thus, with far-bearing animals it has been observed anemia when organic acids have been added to the feed without additional support of folic acid (vitamin $B_9$).

Further it has also been reported in the literature that other B-vitamins may influence the production of blood cells, although the exact mechanisms are not clearly understood. Still, it was considered that vitamins $B_6$ and $B_{12}$ should be good candidates together with vitamin $B_9$. Accordingly, the inventor decided to add said three B-vitamins to the mixture of monocarboxylic acids, comprising formic acid and its ammonium salt in order to investigate if said addition of vitamins could compensate for the previously observed side-effects related to monocarboxylic acids. Iron was also added to the new feed mixture because reduced haemoglobin levels in the blood had been reported in the literature as a sign of iron deficiency. Said organic acids were chosen because of the reported positive effects of monocarboxylic acids.

However, it was found that also other carboxylic acid had advantageous properties in supplements for the present purpose. The above stated mixture was dissolved in water and mixed with the ordinary water intake for the pigeons. When the supplement was dosed at about 1 gram/litre, the pigeons were reluctant to drink the water. The dosage was then reduced to 0.5 gram supplement/litre, at which no reluctancy to drinking was observed. At this dosage the vitamin supplement still was considerably above recommended dosage for vitamin supplement for racing pigeons.

Having been given this supplement for an extended period the pigeons proved to endure stress conditions without problem and performed excellently during even demanding races. Based on the positive results, further similar experiments were started in order to confirm the results and find the correct balance between the components by expanding the experiments to other species than racing pigeons. In view of the results from these experiments it was decided to also add other B-vitamins. It was also considered advantageous to add an antioxidant, preferably vitamin E. An iron component, preferably iron fumarate, should also still be included in the supplement as iron is essential in the production of blood cells. In order to secure a free flowing product a desiccant could be added to the supplement to be further tested, the most preferred desiccant was found to be MgO.

The scope and special features of the invention are as defined by the attached claims.

The main feature of the supplement according to the invention is that it comprise at least one carboxylic and/or its salt as the basic ingredient and the vitamins $B_6$, $B_9$ and $B_{12}$ in total amounts of 10-50 mg/gram dry weight of the supplement, 5-25 mg Fe/gram dry weight of supplement, 0-1 weight % desiccant and 0-1 weight % of an antioxidant, and that the amounts of salt and carboxylic acids will give a pH of 2.0-6.0 when the supplement is dissolved in water.

The amount of vitamins $B_6$, $B_9$ and $B_{12}$ should at least correspond to that which can be consumed during metabolism of the COOH-group of the carboxylic acids.

The supplement should preferably contain 0.5-3.5 weight % iron fumarate.

A special feature of the supplement according to the invention is that the preferred amounts of vitamins $B_6$, $B_9$ and $B_{12}$ are in the range 0.5-30 mg, 0.1-10 mg and 1-1500 µg/gram dry weight of the content of the pure carboxylic acids in the supplement, respectively.

The new supplement should preferably contain vitamin E as antioxidant and MgO as desiccant.

The most preferred carboxylic acids were found to be $C_{1-8}$ carboxylic acids.

The invention also comprises use of the new supplement for improving the performance during stress and competition conditions in amounts of 0.5-15 grams dry supplement/kg dry feed.

A special use of the supplement is its mixture with the standard feed for horses in amounts of 1-15 grams dry supplement/100 kg horse weight.

Use of the supplement in food for humans could be performed by administration of 0.1-4.4 mg daily intake per kilogram bodyweight.

The invention is further explained in connection with the following examples.

EXAMPLE 1

This experiment was performed on racing pigeons belonging to the company Pigeon Vitality as in Porsgrunn Norway. The pigeons were given 0.5 grams/litre water of carboxylic acids in the drinking water having a pH of 4, daily from the autumn 2001 and through the racing season 2002 ending in July. The first races that spring, the pigeons performed below expectation. They returned home several minutes too late for top prizes. Performance became even worse as the racing season went on, and after the first races (two-three weeks) the pigeons lost their level of performance. Three weeks later they showed all signs of anemia. The races were stopped for the test loft in June 2002 after only six races.

Pigeons from the same loft, same location, on the same feeding system, same training, same racing system, same management were part of the new experiment where supplement (same carboxylic acids) at same dosages in the drinking water were upgraded by addition of vitamins $B_6$, $B_9$ and $B_{12}$ and 6 mg iron/kilogram supplement. The racing season turned out to be the best ever for Pigeon Vitality as, with extraordinary good results from start until the last competition six weeks later. The performances are shown in Table 1, comparing results for the two seasons.

TABLE 1

| Race no. | Distance in km (2002/2003) | 2002 score $1^{st}$. pigeon | 2003 score $1^{st}$. pigeon |
|---|---|---|---|
| 1 | 150/100 | 68 | 100 |
| 2 | 200/200 | 43 | 100 |
| 3 | 200/250 | 0 | 94 |
| 4 | 350/300 | 29 | 100 |
| 5 | 400/400 | 0 | 100 |
| 6 | 200/100 | 17 | 85 |
| 7 | Not attending/550 | Not attending | 100 |

The score is calculated such that it can be compared even if the number of attending pigeons in the race may vary. The score S is calculated as $S=100-((P-1)*300)/N$ points, where N is the total number of attending pigeons and P is the placement on the result list of the pigeon race. First prize, will always give 100 points in score. Thereafter the scores fall successively to 1 point given to the bird returning in the last position among the ⅓ best pigeons on the result list. Thereafter scores of 0 will be given to the rest of the pigeons (the next ⅔ of the pigeons that returned as the latest). The table 1 gives the score of the first pigeons for the test loft of Pigeon Vitality AS, clearly indicating a huge improvement in racing performance in the season 2003 as compared to 2002

EXAMPLE 2

The possible effect on the above mentioned erosions in the gastric/intestinal mucosa problem experienced on horses was also investigated. 10 horses having developed erosions in the gastric/intestinal mucosa were fed twice a day. Contrary to the normal procedure they now got 40-50 grams (dry weight) of the new supplement mixed with the normal feed twice a day for 14 days. The horses weighed 450-500 kg and accordingly the addition of supplement corresponds to 10 grams dry weight of the supplement/100 kg horse weight. At the end of this new feeding period gastroscopic examination revealed that the erosions in the gastric/intestinal mucosa had been healed. The horses were therefore allowed to start in a race in which they performed extremely well. All the experiments were performed on sick horses having erosions in the gastric/intestinal mucosa.

In view of further investigations, it was found that the above effect could be achieved by addition of 5-25 grams supplement/100 kg horse weight to the standard feed.

EXAMPLE 3

These experiments were performed on racing dogs (racing dog team) after the above experiments with the pigeons and horses. The experiments started in the autumn of 2003 and the objectives were to find the proper level of dosage, and to take notes of the dog's vitality and fur, together with blood samples. The blood were taken from two test groups, one without any of the new supplement, while the other test group were given 2.5 grams supplement per kilogram feed per day, corresponding to 1.0-1.5 grams supplement per dog (25-35 kg). Blood samples were analyzed with respect to the concentration of blood cells before start, after 2 months and after the end of the racing season. The results of these experiments confirmed that the new supplement gave similar results for dogs as for pigeons and horses. There were no signs of anemia on the dogs and furthermore the level of blood cells was found to be elevated after the test period (6 months). Observation of the vitality of the dogs showed that they were in extremely good shape throughout the test period. Even the fur of the dogs proved to be excellent, resulting in among other a first prize in a large dog show exhibition.

EXAMPLE 4

In addition to the treatment of the erosions in the gastric/intestinal mucosa, the main objective of this example was to find the proper level of dosage, and to take notes of the general observations. All observations were done by veterinarians at Bjerke Dyrehospital in Oslo, a hospital specialized on trotters and gallop horses. Observations of the overall vitality of the horses confirmed that they were in excellent shape after the treatment with organic acids and the selected vitamins.

Furthermore, the 14 horses taking part in the experiments kept their vitality after disease treatment and performed well during and after races. Several improvements were noted as described in Table 2.

TABLE 2

| Observations | Improvements in % of number of tested horses. |
|---|---|
| Appetite | 70% |
| Condition | 85% |
| Well-being | 50% |
| Skin and coat | 30% |
| Pastern dermatitis | 100% |
| Erosions in the gastric/intestinal mucosa | 100% |
| Willingness to train | 50% |
| Racing performance | 50% |
| Imbalances in the gastrointestinal tract | 100% |

From the above examples on various animals, it can be seen that the amount of added vitamins $B_6$, $B_{12}$ and $B_9$, which should at least correspond to the amount of COOH-groups that can be metabolised, have been achieved by the new supplement. Based on the results from all the experiments and information found in the literature, the inventor arrived at the following Table 3 for recommended vitamin content in the supplement according to the invention.

TABLE 3

| Group of species | $B_6$ (mg/kg feed) | $B_{12}$ (μg/kg feed) | $B_9$ (mg/kg feed) | Fe (mg/kg feed) |
|---|---|---|---|---|
| Poultry | 1-7.4 | 15-40 | 0.5-4 | 80-90 |
| Pigeons | 1-5 | 20 | 1 | — |
| Pigs | 3-6.2 | 20-60 | 0.6-5 | 57-62 |
| Cattle | 4-6.2 | 30-50 | — | 30-40 |
| Sheep | — | 15 | 2 | 30 |
| Fish | 8-12.3 | 30-50 | 4-10 | — |
| Horses | 3-3.7 | 20 | 10 | 40-100 |
| Rabbits | 1-1.2 | 5 | 0.2-0.5 | — |
| Maximum(average) | 12 | 60 | 10 | 100 |
| Supplement to feed (2.5gram/kg feed) | 41 | 500 | 45 | 32 |
| Supplement to water (0.5gram/litre) | 10 | 120 | 11 | 8 |

The recommendations for addition of vitamins to various species are given as vitamin supplement per kg feed and in accordance with this the vitamin amounts are shown using the new supplement per kg feed (the 2 last rows in Table 3). The addition of supplement are given for two dosages, 2.5 grams/kg feed, and 0.5 grams per litre water for pigeons, respectively. The dosage from litre water to kg feed is calculated from the knowledge that a pigeon on the average drink 50 ml water and eat 40 grams feed per day.

EXAMPLE 5

It is known from the literature that organic acids may have a benefit to rheumatism. Furthermore the combination of the three B-vitamins $B_6$, $B_9$ and $B_{12}$ has been described as a possible remedy against depressions (Refs.; Taylor M J. et al. The Cochrane Library, Issue 2, 2003; Hintikka J et al. BMC Phsychiatry 2003; 3-17). Thus there was an interest to test out the combination according to the present invention in a preliminary study on humans. The experiments were performed by a group of 10 people all suffering from either rheumatism or depression, or a combination of these.

The persons were given the supplement once daily for more than three weeks, and the persons reported their experiences after this period. The main organic acids in the supplement were formic acid and ammonium formate, dosed as to fit the acceptable daily intake of 3 mg per kilogram body weight. The content of vitamins were within that recommended for humans as e.g. by the "The Vitamin Revolution" by Knut T. Flytlie, Hilt & Hasten, ISBN 82-7413-566-0, and according to the authorities (Nordic, EU and USA) recommendations for daily and tolerance levels, although the content of folic acid and vitamin $B_{12}$ were elevated due to the expected interaction with the organic acids. However according to medical literature it has not been reported any negative bieffects for adults who have had an intake of either 400 mg/day of $B_9$ during 5 months or 10 mg/day during 5 years.

All reports were positive. The pain from the rheumatism disappeared and a remarkable high spirit and good humor prevailed. Furthermore the test persons reported increased vitality and better sleep at night. No negative effects were observed or reported, although two persons reported "unstable stomach" the first two-three days, but then again returned to normal. The applied vitamin dosages of the daily intake of the supplement are shown in Table 4.

TABLE 4

| Human | $B_6$ (mg/day) adult/child | $B_9$ (μg/day) adult | $B_9$ (μg/day) child & pregnant | $B_{12}$ (μg/day) adult/child |
|---|---|---|---|---|
| Contraceptive | 4/1 mg | 200 μg | Infant 30 μg | 3/1 μg |
| Long term prophylactic | 8/2 mg | 400 μg | Small children 50 μg | 5/2 μg |
| Support treatment | 50/4 mg | 800 μg | School children 100 μg | 50/2 μg |
| General treatment | 250/8 mg | Max 1500 μg | Pregnant 800 μg | 100/3 μg |

EXAMPLE 6

A number of tests were made on pigeons, human, horses and dogs in order to confirm the amounts of B-vitamins and iron to the various species. The supplement used during these tests contained 330 mg formic acid/formates and 60 mg lactic acid per gram supplement. The results of these tests are shown in Table 5 and states the average values for the respective vitamins for the various species. The values are given as mg vitamin/day per gram 100% formic acid/formates per kilogram body weight.

TABLE 5

| Component | Pigeon | Human | Horse | Dog |
|---|---|---|---|---|
| $B_6$ | 1.55 | 0.33 | 1.24 | 0.62 |
| $B_9$ | 2.05 | 0.44 | 1.64 | 0.82 |
| $B_{12}$ | 0.0095 | 0.0020 | 0.0076 | 0.0038 |
| Fe | 2.5 | 0.5 | 2.0 | 1.0 |

The recommended amounts of the new supplement will vary depending on species and their age, and duration of treatment. Generally 2.5 gram supplement per kg feed is considered optimal, but amounts of 0.5-15 grams dry supplement/kg feed were found to give the desired results. The upper range will in most cases represent an over-dosage and this will be on purpose for extreme conditions as they generally require extra feed and vitamin supply or on purpose for the early phase of treatment. All the B-vitamins are water soluble and any excess will be excreted. Another reason for securing that one is on the safe side is that the level of metabolic oxidation of carboxylic acids vary from species to species and still is not fully understood scientifically.

The recommended supply of iron will depend on the activity of the species. As iron is widely distributed in the feed in question, and because the efficiency of absorption of iron is increased during periods of need and therefore the above formulations are relatively low compared to that generally recommended. During these experiments iron fumarate has been used as iron source and it contain 32% iron. This has been corrected for in Table 3. The recommendable amounts of iron in the supplement were found to be in the range of 5-25 mg Fe/gram dry supplement, preferably in the range 10-15 mg Fe.

The carboxylic acid/salt mixture used during the experiments comprise formic acid, ammonium formate and lactic acid. According to our experiments the dosage of organic acids for prophylactic treatment may vary from species to species; e.g. ranging from human 3 mg/day per bodykilogram to 50 mg/day per bodykilogram for horses. It was found that the vitamins should preferably be added as vitamin B-complexes since all B-vitamins (i.e. all B-vitamins, including $B_6$, $B_9$ and $B_{12}$) are incorporated in various enzyme systems, and because their interactions and metabolic routes are not clearly understood. However, as shown above, it is essential that vitamins $B_6$, $B_9$ and $B_{12}$ are present in the recommended amounts. Accordingly, based on our experiments on birds, animals and humans, the amount of vitamin $B_6$ in the new supplement should be in the range 0.1-2 mg/daily dose per bodykilo, $B_9$ in the range 0.2-2.5 mg/day per bodykilo, and $B_{12}$ in the range 1-10 μg/day per bodykilo.

As supplement the vitamins $B_6$, $B_9$ and $B_{12}$ usually correspond to 3-10% of the various B-vitamin complexes designed for animal and human use. Said vitamins can also be added in the form of known ingredients having relatively high concentration of said vitamins.

The most useful carboxylic acid were found to be $C_{1-8}$ carboxcylic acids and the most preferred acids would be formic-, citric-, lactic-, propionic-, ascorbic-, fumaric- and benzoic acid. It was also found that salts of said acid advantageously could be used, especially in order to give the supplement the desired pH. Mixture of such acid and salts could be used. The new supplement should preferably be in dry powder form making the supplement free flowing. Useful desiccants would be silica MgO, CaO, etc., provided they are acceptable in feed for animals and human. The new supplement may contain antioxidants like antho-cyanin, tocopherol (vitamin E), astaxanthin and carotenoids for delaying the oxidation degradation. Optionally the new supplement may contain minerals containing K, Ca, Fe, Mg and other standard nutrients etc in cases where the standard feed are deficient in these elements. The above new supplement was found useful for especially horses, dogs, pigeons and human t. However, other animals exposed to similar problems can benefit accordingly by fed this supplement. If the supplement is applied in connection with fish farming it should be mixed with the standard feed and it is then essential that said mixture can be performed without changing the composition of the supplement. Even human consumption caused no problem and seemed only to be beneficial.

Theoretically the various components of the new supplement could be added one-by-one to the standard feed of the consumer. However, such a procedure would cause great practical problems in applying correct amounts of the various ingredients. Further, it might be difficult to obtain the observed interaction between the components.

The invention claimed is:

1. A food and feed supplement containing vitamins, for improvement of health and performance, the supplement comprising
   at least one $C_{1-8}$ carboxylic acid and/or its salt as the basic ingredient wherein the $C_{1-8}$ carboxylic acid is a formic acid, a citric acid, a lactic acid, a propionic acid, an ascorbic acid, a fumaric acid, an acetic acid or a benzoic acid; and vitamins B6, B9 and B12 which are present in the range of 0.5-30 mg, 0.1-10 mg and 1-1500 μg/gram dry weight of the at least one carboxylic acid and/or its salt, respectively, wherein
   the $B_6$, $B_9$ and $B_{12}$ vitamins are present in a combined amount of 10-50 mg/gram dry weight of the supplement to compensate for the loss of the $B_6$, $B_9$ and $B_{12}$ vitamins due to carboxylic acid metabolism;
   5-25 mg Fe/gram dry weight of the supplement;
   0-1 mg of an antioxidant per 100 mg dry weight of the supplement; and the amount of the carboxylic acid and/or its salt will give a pH of 2.0-6.0 when the supplement is dissolved in water.

2. Supplement according to claim 1, characterized in that it contains 0.5-3.5 mg of iron fumarate per 100 mg dry weight of the supplement.

3. Supplement according to claim 1, characterized in that the supplement contains vitamin E as an antioxidant.

4. Supplement according to claim 1, characterized in that it contains a desiccant.

5. A method for improving the performance of an animal during stress and competition conditions, the method comprising:
   administering to the animal the supplement of claim 1 in an amount of 0.5-15 grams dry supplement/kg dry feed.

6. A method for improving the performance of a horse during stress and competition conditions, the method comprising:
   administering to the horse 1-15 grams dry weight of the supplement of claim 1 per 100 kg horse weight in a standard feed for horses.

7. A method of improving performance of a human during stress and competition conditions, the method comprising:
   administering to the human 0.1-4.4 mg daily of the dry weight of the supplement of claim 1 per kilogram bodyweight.

8. The supplement of claim 1, wherein the $B_6$ vitamin is in an amount of 0.07-24.6 mg/gram dry weight of the supplement.

9. The supplement of claim 1, wherein the $B_9$ vitamin is in an amount of 0.01-20 mg/gram dry weight of the supplement.

10. The supplement of claim 1, wherein the $B_{12}$ vitamin is in an amount of 0.33-120 μg/gram dry weight of the supplement.

* * * * *

UNITED STATES PATENT AND TRADEMARK OFFICE
CERTIFICATE OF CORRECTION

PATENT NO. : 7,815,930 B2  
APPLICATION NO. : 10/596224  
DATED : October 19, 2010  
INVENTOR(S) : Frode Brakstad et al.

It is certified that error appears in the above-identified patent and that said Letters Patent is hereby corrected as shown below:

Column 9, Line 9, Claim 1:

Delete "B6, B9 and B12" and insert -- $B_6$, $B_9$ and $B_{12}$ --.

Signed and Sealed this  
Twenty-fifth Day of January, 2011

David J. Kappos  
*Director of the United States Patent and Trademark Office*